US00PP26335P2

(12) United States Plant Patent
Boehm

(10) Patent No.: US PP26,335 P2
(45) Date of Patent: Jan. 19, 2016

(54) ***SCHIZACHYRIUM* PLANT NAMED 'PRAIRIE MUNCHKIN'**

(50) Latin Name: *Schizachyrium scoparium*
Varietal Denomination: Prairie Munchkin

(71) Applicant: Don L. Boehm, Rushville, IL (US)

(72) Inventor: Don L. Boehm, Rushville, IL (US)

(73) Assignee: PLANTS NOUVEAU, LLC, Mobile, AL (US)

( * ) Notice: Subject to any disclaimer, the term of this patent is extended or adjusted under 35 U.S.C. 154(b) by 163 days.

(21) Appl. No.: 13/998,401

(22) Filed: Oct. 29, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Anne Grunberg
(74) *Attorney, Agent, or Firm* — Penny J. Aguirre

(57) ABSTRACT

A new cultivar of *Schizachyrium scoparium*, 'Prairie Munchkin', that is characterized by its upright plant habit that does not lodge, its foliage that is blue in color changing to a maroon-orange color in the fall, and its height of 90 cm in bloom.

2 Drawing Sheets

Botanical classification: *Schizachyrium scoparium.*
Varietal denomination: 'Prairie Munchkin'.

BACKGROUND OF THE INVENTION

The present invention relates to a new and distinct cultivar of *Schizachyrium scoparium* and will be referred to hereafter by its cultivar name, 'Prairie Munchkin'. 'Prairie Munchkin' represents a new cultivar of little bluestem, an ornamental grass grown for landscape use.

The Inventor discovered the new cultivar, 'Prairie Munchkin', in June of 2006, as a chance seedling growing outdoors in his trial garden in Rushville, Ill. The trial garden had been planted with a mix of seeds derived from the open pollination of 'Carousel' (U.S. Plant Pat. No. 20,948) and unnamed proprietary *Schizachyrium scoparium* seedlings derived from 'Carousel' (not patented).

Asexual propagation of the new cultivar was first accomplished by culm division in Union, Ill. in June 2010 by the Inventor. Asexual propagation by culm division and tissue culture has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Prairie Munchkin' as a new and unique cultivar of *Schizachyrium scoparium.*

1. 'Prairie Munchkin' exhibits an upright plant habit that does not lodge.
2. 'Prairie Munchkin' exhibits foliage that is blue in color changing to a maroon-orange color in the fall.
3. 'Prairie Munchkin' exhibits a height of 90 cm in bloom.

'Prairie Munchkin' can be most closely compared to *Schizachyrium* cultivars 'Carousel', 'MinnBlueA' (U.S. Plant Pat. No. 17,310) and 'The Blues' (not patented). 'Carousel' is similar to 'Prairie Munchkin' in having foliage that is blue in color. 'Carousel' differs from 'Prairie Munchkin' in having an open arching plant habit that is prone to lodging. 'The Blues' is similar to 'Prairie Munchkin' in having foliage that is blue in color and changes to a similar maroon-orange color in the fall. 'The Blues' differs from 'Prairie Munchkin' in having a less upright plant habit, in being taller in stature, in being prone to lodging, and in having a lower tolerance for average garden soil with high fertility. 'MinnBlueA' is similar to 'Prairie Munchkin' in tolerating fertile soils, in not lodging, and in having uniquely colored fall foliage. 'MinnBlueA' differs from 'Prairie Munchkin' in being much taller in height and in having purple, pink, and red foliage coloration in fall.

BRIEF DESCRIPTION OF THE DRAWINGS

The accompanying colored photographs illustrate the overall appearance and distinct characteristics of the new *Schizachyrium.*

The photograph in FIG. 1. was taken of a plant about 2 years in age as grown outdoors in Rougemont, N.C. in a 3-gallon container and provides a view of the summer foliage and blooming habit.

Figure 1:
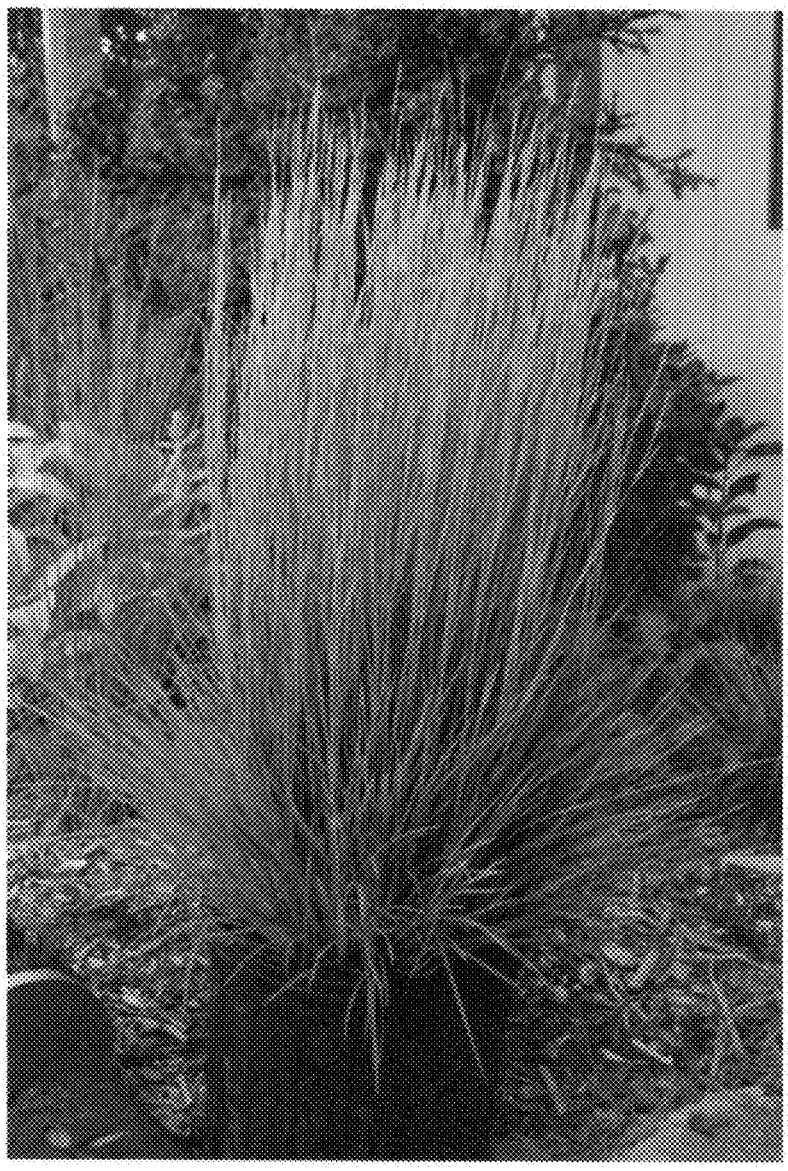
Figure 2:
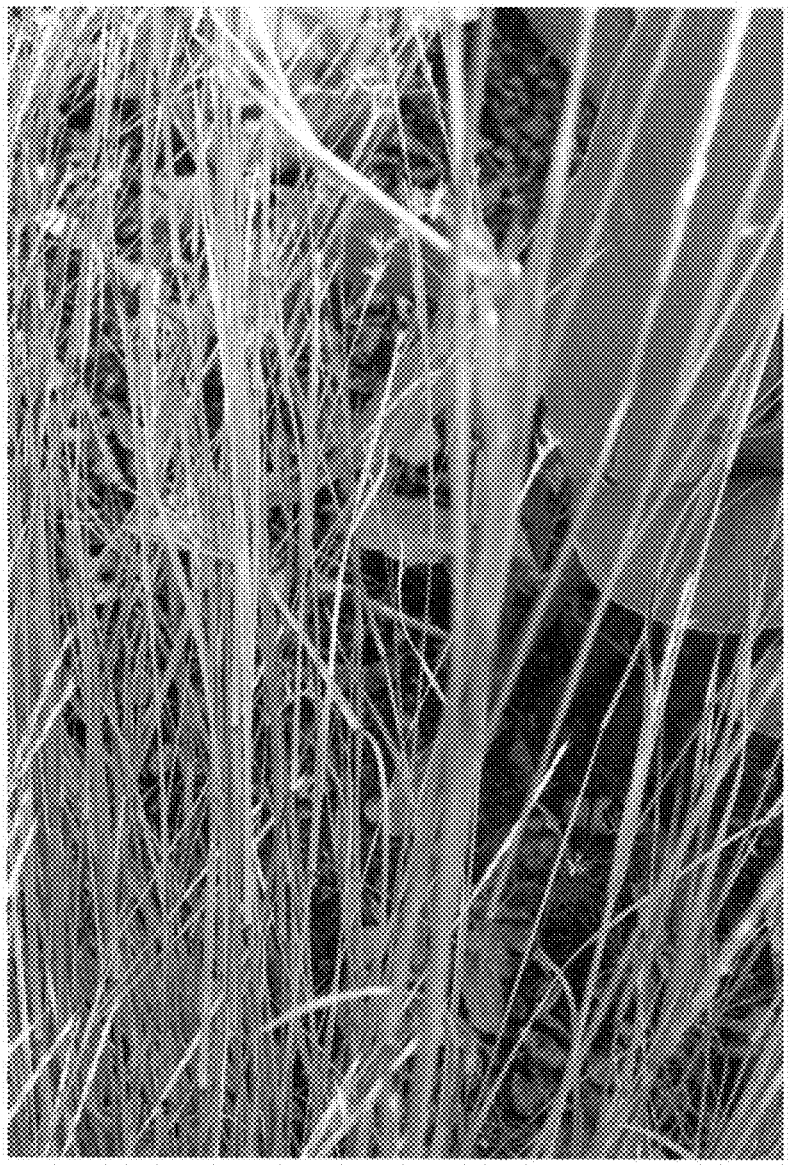

The photograph in FIG. 2. was taken of a plant about 3 years in age as grown in a garden in Rushville, Ill. and provides a view of the fall foliage.

The colors in the photographs are as close as possible with the photographic and printing technology utilized and the color values cited in the detailed botanical description accurately describe the colors of the new *Schizachyrium.*

DETAILED BOTANICAL DESCRIPTION

The following is a detailed description of 2 year-old plants as grown outdoors in a 2-gallon container in Union, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—August to November in Illinois with seed heads persistent.

*Plant type*.—Herbaceous, perennial grass.

*Plant habit*.—Upright, erect stems that do not lodge.

*Height and spread*.—An average of 90 cm in height and 45 cm in spread when mature in the landscape.

*Hardiness zone*.—U.S.D.A. Zones 3 to 9.

*Diseases and pests*.—*Schizachyrium scoparium* is relatively free of disease. No susceptibility or resistance to disease or pests has been observed.

*Root description*.—Fibrous, wiry, deep rooted.

*Propagation*.—Culm division and tissue culture.

*Growth rate*.—Moderate.

Culm (stem) description:

*General*.—Cylindrical, solid, held erect.

*Culm color*.—164A in summer, a blending of 164A, 164C, and 176B in fall, 161A in winter, about 3.5 cm of exposed area between leaf nodes.

*Culm size*.—Average of 2 mm in diameter, averaging 30 cm in height from the base to the base of the terminal flower panicle.

*Culm surface*.—Glabrous.

*Internode length*.—Average of 7 cm.

Foliage description:

*Leaf shape*.—Linear, sheathed with a leaf blade extending from ligule at nodes.

*Leaf division*.—Simple, margins entire.

*Leaf base*.—Sheathed to base of the node.

*Leaf venation*.—Parallel, not distinguishable in color from leaf.

*Leaf size*.—Basal leaves average of 15 cm in length and 3 mm in width, culm leaves an average of 15 cm (sheathed portion 5.5 cm) and 5 mm in width and 10 cm (sheathed portion 3.5 cm) in length and 3 mm in width near the apex.

*Leaves per culm*.—Average of 4.

*Leaf surface*.—Glabrous on outer and inner surface.

*Ligule*.—1 mm in width, membranous, 158B in color.

*Leaf color*.—Summer; 147B, fall; a blend of 184B to 174C to N186D, winter; 161D to 158A.

Flower description:

*Inflorescence*.—An average of 8 per culm, 1 to 4 racemes present per node, typically on upper 4 nodes, last about 2 weeks, about 5 cm in length and 8 mm in width. Rachis is about 12 cm in length and 0.3 mm in width with racemes of spikelets arranged alternately on upper 5 cm. Spikelets are appressed to the rachis and appear sessile, rachis is 138B in color and the overall mature color of the raceme is 161D.

*Spikelet description*.—Average of 8 per raceme, equal glumes 7 mm in length and 1 mm in width and 138B in color, lemma extending into very fine flexuous awn, 5 mm in length 144B in color with fine awn about 8 mm in length, palea small and hyaline.

*Spikelet size*.—About 1.8 cm in length with awn and 1 mm in width.

*Spikelet hairs*.—Emerging from the base as a tuft, average of 4 mm in length, very fine, 155B in color.

Reproductive organs:

*Androecium*.—Anthers; 3, 3 mm in length and 0.7 mm in width, 145C in color, basifixed on very fine filament extending about 1.5 mm from spikelet, Pollen; none observed to be present.

*Gynoecium*.—Pistil; 1, quickly fleeting, 2 plumose stigmas on short, file styles, stigma color is 155A, 2 mm in length and 1 mm in width, ovary; 1-locular, superior, minute, not easily quantifiable in size and color.

*Caryopsis*.—Lemma and palea adhering to the caryopsis, actual caryopsis very small and fine, less than 1 mm.

It is claimed:

1. A new and distinct cultivar of *Schizachyrium* plant named 'Prairie Munchkin' as herein illustrated and described.

* * * * *